(12) United States Patent
Stalcup et al.

(10) Patent No.: US 6,344,121 B1
(45) Date of Patent: Feb. 5, 2002

(54) PREPARATIVE CHIRAL SEPARATIONS

(75) Inventors: Apryll Marie Stalcup, Cincinnati, OH (US); Richard Matthew Charles Sutton, Camberley (GB)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/448,789

(22) Filed: Nov. 24, 1999

Related U.S. Application Data

(60) Provisional application No. 60/109,755, filed on Nov. 25, 1998.

(51) Int. Cl.[7] ............................................. G01N 27/26
(52) U.S. Cl. ........................................ 204/456; 204/450
(58) Field of Search ................................ 204/450–452, 204/456, 461, 466

Primary Examiner—Jill Warden
Assistant Examiner—Alex Noguerola
(74) Attorney, Agent, or Firm—Dinsmore & Shohl LLP

(57) ABSTRACT

The methods of the present invention address a critical need for the development of preparative chiral separations. These include preparative chiral separation methods based on continuous electrophoresis using a chiral additive in the buffer. The application of continuous free flow electrophoresis to bulk scale aqueous chiral separations is novel and has the potential for obtaining mg to g/hour quantities of both pure enantiomers of chiral drugs in aqueous solution, with wide applicability for a broad range of chiral drugs from many different categories as well as chiral intermediates or metabolites. The present methods allow for the potential recovery and reuse of the chiral selector (typically expensive and/or rare). Although continuous free flow electrophoresis has been used primarily for the separation of biopolymers, its use for the separation of small molecules has remained relatively unexplored.

44 Claims, 7 Drawing Sheets

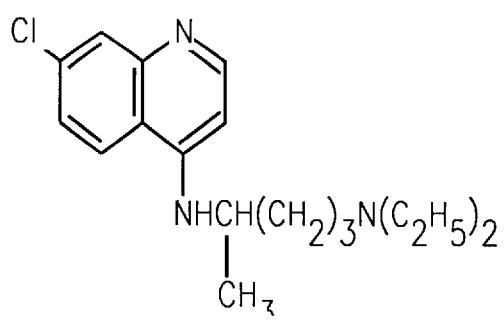
Figure 7 (a)
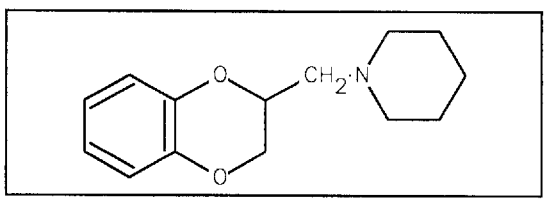
Figure 7b. Structure of piperoxan
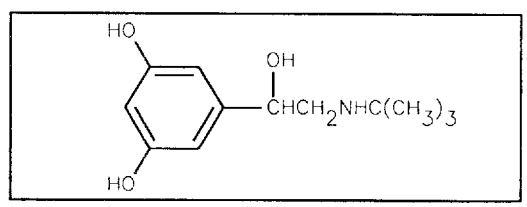
Figure 7c. Structure of terbutaline

PREPARATIVE CHIRAL SEPARATIONS

This application claims priority from Provisional Application No. 60/109,755 filed Nov. 25, 1998.

This invention was made in part with Government support under Grant No. GM48180-05 awarded by the National Institutes of Health. The Government may have certain rights in this invention.

FIELD OF THE INVENTION

The invention relates to methods for preparative chiral separation. More particularly, the present invention relates to continuous free-flow electrophoresis preparative chiral separation by addition of chiral auxiliary agent(s).

BACKGROUND OF THE INVENTION

Separation of enantiomers is an important topic to the pharmaceutical industry. Many of the drugs marketed in the U.S. have at least one chiral center (e.g., ibuprofen and propranolol). Of the 528 synthetically derived chiral drugs, 88% are sold as the racemic mixture. The biological activities and bioavailabilities of the enantiomers sometimes differ. Often, one enantiomer has the desired therapeutic activity whereas the other enantiomer causes undesirable side-effects and may limit drug efficacy or dosage. It is also possible for both enantiomers to have therapeutic value . . . just not for the same disease state. For example, (S)-verapamil is effective as a calcium channel blocker while (R)-verapamil produces cardiac side effects but has potential in reversing multiple drug resistance in cancer therapy. Thus, the development of economical methods for preparative and semipreparative scale chiral separations is highly desirable.

Chiral separations are commonly performed using chiral stationary phases by liquid chromatography (HPLC), first reported in the early 1980's. The last decade has seen the commercialization of many different types of chiral stationary phases for HPLC. Each of these chiral stationary phases is very successful at separating large numbers of enantiomers which, in many cases, are unresolvable using any other chiral stationary phase. However, a large number of chiral compounds are unresolvable using any of the existing chiral stationary phases. Chiral HPLC columns are more expensive and require more careful handling than conventional columns. Column deterioration often results from a loss of the bonded phase rather than decomposition or racemization of the chiral ligand. Once the chiral column has begun to deteriorate, it generally cannot be returned to its original performance levels. Lot-to-lot variability further hampers method development and large-scale chiral separations remains largely unexplored.

Incomplete understanding of the chiral recognition mechanisms for many of these chiral stationary phases hinders rapid method development. Mobile phase optimization for many chiral HPLC stationary phases is usually not a trivial problem. In conventional HPLC, the relationship between retention and mobile phase composition or column temperature is well-behaved. However, for many chiral stationary phases, normal phase type-behavior may result under very nonpolar mobile phase conditions and reversed-phase behavior under very polar conditions. Often, there is a narrow "window" of mobile phase conditions under which enantioselectivity is observed and these conditions are usually solute-specific. In contrast to achiral chromatography, there are no chiral TLC plates (except ligand exchange chiral plates) commercially available for scouting mobile phase conditions or likelihood of chiral separation. Thus, column and conditions selection is often reduced to identifying structurally similar analytes for which chiral chromatographic methods have been reported in the scientific literature or chromatographic supply catalogues, and adapting the method for the chiral pair to be resolved.

Preparative chromatography (prep LC), often the method of choice for preparative chiral separations, requires the availability of a suitable chiral stationary phase (CSP). Prep LC columns are also costly and are usually only commercially available on a "special order" basis. Lot-to-lot variability in the packing sorbent as well as non-linear adsorption isotherms (e.g., in situ generation of secondary "chiral phase" from sorbed enantiomer) arising from mixed mode adsorption complicate scale-up. In addition, the mode of chromatography (e.g., batch vs displacement vs recycling vs simulated moving bed) must be decided.

Bioavailability of drug substances dictates that the compounds be water soluble and many are ionized at physiological pH. The $pK_a$'s of many drugs are well outside the safe operating range for silica-based media (Table 1) and almost all chiral stationary phases currently available are on silica substrates.

Most prep chiral LC employs an organic mobile phase. Many underivatized chiral drugs have only limited solubility in these organic mobile phases. Thus, sample

TABLE 1

Examples of $pK_a$'s for various chiral drugs

| Drug | Class | $pK_a$ |
|---|---|---|
| albuterol | bronchodilator | 9.3 |
| bupivacaine | anesthetic | 8.1 |
| chloroquine | antimalarial | 10.8, 8.4 |
| chlorpheniramine | antihistamine | 9.2 | introduction for many native drugs onto preparative chiral chromatographic columns often requires that packing material be removed from the head of the column, the sample mechanically mixed with this packing material. This mixture is then added to the top of the column, a process which is not easily automated.

Alternative techniques such as counter-current and centrifugal partition chromatographic methods, while allowing chiral selector recovery, require considerable amounts of mobile phase. Stereospecific enzymatic degradation requires identification of a suitable enzyme and often, a complementary enzyme is not available. Enzymatic degradation often preferentially destroys one enantiomer which may have intrinsic value or serve as an internal standard or reference material.

Among the most successful of the liquid chromatographic reversed-phase chiral stationary phases have been the cyclodextrin-based phases. Under predominantly aqueous mobile phase conditions, the mechanism responsible for the chiral selectivity with these phases is thought to rely on inclusion complexation between a hydrophobic moiety of the chiral analyte and the interior of the cyclodextrin cavity. Preferential complexation between one optical isomer and the cyclodextrin results in enantiomeric separation. However, selectivities ($\alpha$) reported for native cyclodextrin phases in the reversed-phase mode are, in general, less than 2.0 perhaps as a consequence of the low surface concentration of the cyclodextrins (e.g., 0.2–0.3 $\mu mol/m^2$).

Classically, electrophoresis has been applied to the separation of charged materials such as proteins, nucleic acids, and cells. The separations depend upon differences in charge density and size. Capillary electrophoresis is a well-known technique for the analytical scale separation of chemical components. A sample solution containing molecules to be separated is introduced at one end of a length of capillary tubing containing an electrophoretic medium. Upon application of an electric field across the capillary, different components within the sample migrate at distinct rates towards the oppositely charged end of the capillary dependent upon their relative electrophoretic mobilities in the electrophoretic medium. Due to the varying electromigratory rates, the sample components become increasingly separated into distinct zones or groups as they progress along the capillary. At some position along the capillary, the components of the sample are detected. For example, U.S. Pat. No. 5,061,361 relates to a capillary zone electrophoresis system in which a nanoliter volume of sample is introduced into the capillary tube, and an electric field is imposed on the system to effect separation of the charged components. After migration along the length of the tube, the sample components are detected via ultra-violet absorbance. U.S. Pat. No. 5,084,150 relates to an electrokinetic method of separation in which the surface of moving charged colloidal particles is treated so as to interact selectively with the sample molecules to be separated. The above-described U.S. patents are hereby incorporated by reference.

Recently, capillary electrophoresis (CE) has been shown effective for chiral separations. Chiral separations by CE are usually accomplished using chiral additives in the run buffer. This approach offers several advantages (e.g., additive can be readily changed, a variety of chiral selectors available, rapid screening of chiral selectors, analytes and conditions, small amounts of background electrolyte required, small amounts of chiral additive required, no preequilibration, multiple complexation possible, faster method development than for HPLC). Unfortunately, CE is generally more suited to analytical separations than to preparative scale separations.

Classical gel electrophoresis, a mature method used extensively for protein and nucleic acid purification and characterization has not been routinely used for small molecule separations presumably because small solutes begin to diffuse away from the band center as soon as the applied voltage is removed. Although detection is usually accomplished off-line in electrophoretic and thin layer chromatographic methods, solute affinity for the chromatographic bed and the immediate removal of the mobile phase following the chromatographic run minimizes solute diffusivity in TLC. In contrast to TLC, the gel matrix serves primarily as an anticonvective medium in gel electrophoresis and is designed to minimize interactions with the solute, excluding molecular sieving effects. Hence, there is no mechanism to localize the solute post-run thereby reducing separation efficiency and complicating detection. However, Stalcup et al. demonstrated that analytes complexed with a bulky chiral additive (e.g., sulfated cyclodextrin, MW~2500), through predominantly electrostatic interactions effectively reduce solute diffusivity to enable enantioseparation using classical gel electrophoresis. Stalcup and co-workers used CE for method development of gel electrophoresis for semi-preparative scale chiral separations.

It should be noted that gel electrophoresis employs less hazardous aqueous solvents than the hydroorganic or organic solvents typically used in most chromatographic-based preparative separations and is less costly in terms of disposal. In addition, costly chiral selectors may be retrieved subsequent to the separation. However, classical gel electrophoresis is a batch process with limited sample throughput.

Preparative continuous free flow electrophoresis translates the tremendous resolving power of electrophoresis into a continuous feed process. Historically, free flow electrophoresis has been used for fractionating charged species such as cells and macromolecules. Free flow electrophoresis is a process in which a sample stream is introduced into a continuous liquid buffer flow at the top of a thin, rectangular electrophoresis chamber while an electric field is imposed perpendicular to the flow within the separation chamber. A fixed or varying electric field is maintained across the separation column perpendicular to the buffer flow. Differential interaction between the various sample components and the electric field produce a lateral displacement of the individual sample components between the two electrodes, dependent upon their charge to weight ratio. Individual sample components can be collected at the opposite end of the chamber using multiple collection ports. Free flow apparatuses are described in U.S. Pat. Nos. 5,562,812, 5,277,774, and 5,082,541, incorporated herein in their entirety.

The angle of the deflection ($\Theta$) of the solute in the electric field is dependent upon the intrinsic electrophoretic mobility of the solute ($\mu_i$), the linear velocity of the buffer (v) and the current through the chamber (i) and can be described as:

$$\tan\Theta = \frac{\mu_i i}{q\kappa v} \qquad (I)$$

where q is the cross section of the separation chamber and κ is the specific conductance of the buffer. The application of (I) to the special case of chiral separations will be discussed in more detail in the Experimental Methods and design.

Despite the use of cooling, microgravitational environments, density and pH gradients, parasitic convection and heat dissipation produced flow stream instability and limited the utility of this approach. However, recent innovations in the design of a continuous free flow electrophoresis apparatus have circumvented the heat dissipation and sample stream distortion inherent in most previous designs. The design exploits the heat exchange capacity of capillary columns by aligning TEFLON capillary tubes close to each other in the electrophoretic chamber. Coolant is pumped through the capillary columns during the electrophoretic run. The system has been used for the separation of biopolymers (e.g., ovalbumin and lysozyme)[1] as well as smaller inorganic species (e.g., $[Co^{III}(sepulchrate)]^{3+}$ and $[Co^{III}(CN)_6]^{3-}$). The inclusion of capillary tubes for cooling allows the chamber cross-section to be increased, thereby allowing for fairly high sample throughput. Sample processing rates of 15 mg/hr were reported for a mixture of Amaranth (MW: 804) and Patent Blue VF (MW: 1159).

The magnitude and frequency of the primary electric field, the rate of primary buffer flow, and the frequency of membrane movement are all dependent on the size of the fractionation chamber being used and the electrophoretic mobilities of the species to be separated. Generally, the species being separated are known species so that their mobilities are known. Once a particular size of a fractionation chamber is chosen it is well within the skill of the artisan to optimize the electric field, the rate of primary buffer flow and sample feed to effect the separation of interest.

The present methods disclose a novel approach to preparative chiral separations. The separation of chiral solutes is accomplished according to the present invention by exploiting differences in electrophoretic velocity between chemical species. Complexation between a chiral solute and a chiral additive essentially modifies the intrinsic electrophoretic velocity or mobility of the solute by conferring some of the intrinsic electrophoretic character of the additive on the solute. The extent of electrophoretic mobility modification is dependent upon several factors including the relative sizes and charge densities of the solute and the additive as well as the affinity of the solute for the additive.

BRIEF DESCRIPTION OF THE DRAWINGS

FIG. 7 illustrates the chemical structures of (a) chloroquine; (b) piperoxan; and (c) terbutaline.

DETAILED DESCRIPTION

Figure 1:
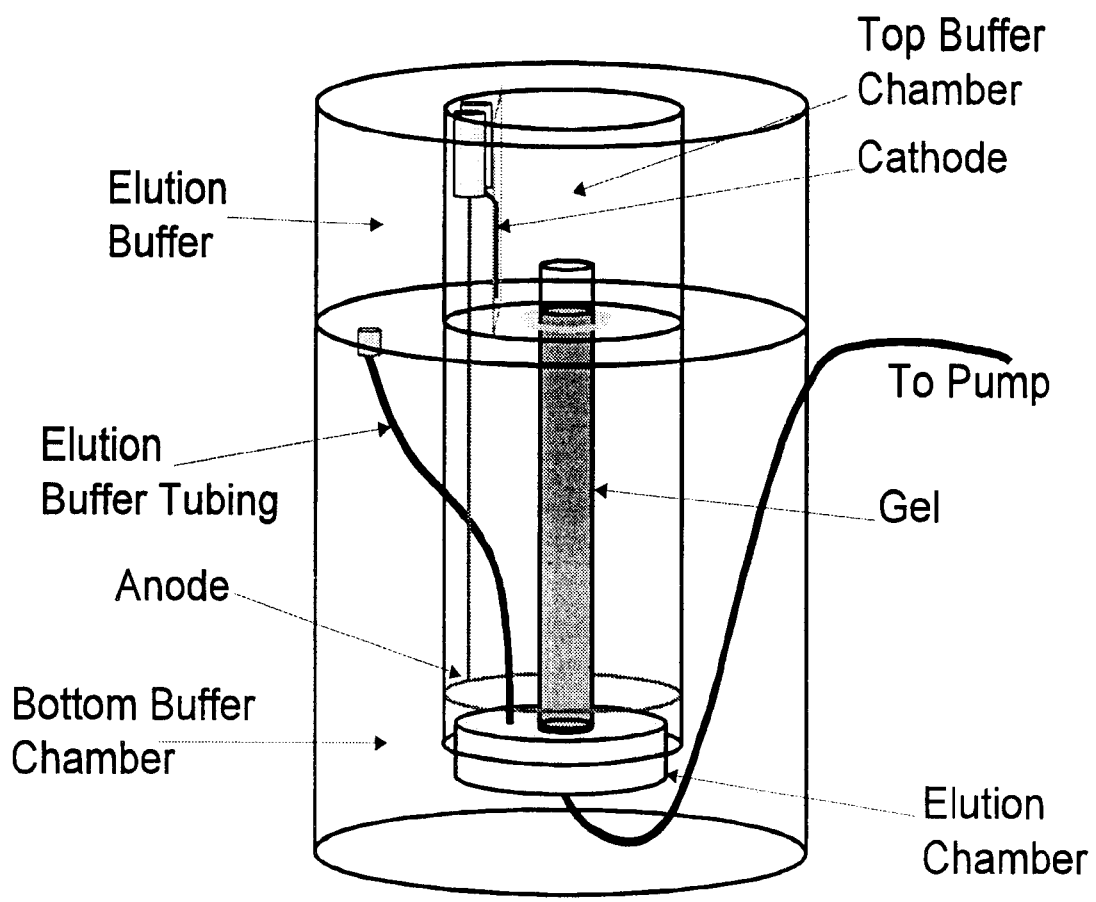
FIG. 1 is a schematic of a mini-preparative continuous elution electrophoresis apparatus.

The methods of the present invention address a critical need for the development of preparative chiral separations. These include preparative chiral separation methods based on continuous electrophoresis using a chiral additive in the buffer. The application of continuous free flow electrophoresis to bulk scale aqueous chiral separations is novel and has the potential for obtaining mg to g/hour quantities of both pure enantiomers of chiral drugs in aqueous solution, with wide applicability for a broad range of chiral drugs from many different categories as well as chiral precurors, intermediates or metabolites. The present methods allow for the potential recovery and reuse of the chiral selector (typically expensive and/or rare). Although continuous free flow electrophoresis has been used primarily for the separation of biopolymers, its use for the separation of small molecules has remained relatively unexplored.

Preferably, There are very few known methods of continuous multi-component separation. Among them, free flow electrophoresis is now gaining popularity. The present invention is related to the group of separation methods represented by free flow electrophoresis using chiral separators. In free flow continuous electrophoresis, a mixture is introduced, at a certain point, into a flow of a liquid, usually, a solution of salts in water. The components are carried with the flow toward the other end of the device. They separate under the influence of a transversal electrical field. The components move along diverging trajectories and are collected with an array of multiple outlets. The use of electrical current in this method narrows the field of its application to water solutions and other electrically conductive liquids.

The use of a charged additive as the carrier in this system will allow for the enantioresolution of not only charged solutes but neutrals as well because the sample stream is introduced independent of the buffer stream and can therefore be tailored, to accommodate the solute.

In various forms of electrophoretic separations involving complexatory additives in the electrophoretic medium, electrophoretic mobility is determined by the charge density of the analyte as well as the degree of complexation with an uncharged additive or charged additive possessing its own electrophoretic mobility. The availability of different electrophoretic media allows various physical properties of analyte or reactant to be exploited so as to vary its electrophoretic velocity. This, in turn, allows the components to electromigrate at different rates in an electric field.

To use electrophoresis for separating large quantities of materials to prepare useful and marketable quantities of separated materials, it is necessary to employ a means of continuous flow electrophoresis. Various systems and methods have been proposed to facilitate continuous electrophoresis separation in various flow-through systems of either a stationary free flow type or moving wall (usually continuous belts) type or single rotating cylindrical wall type. In each of these devices, a buffer, or carrier, liquid is introduced at one end of a thin cross section chamber and drawn off at the other end to create a flowing curtain of liquid between a pair of electrodes of opposite polarity forming at least a portion of the confining walls of the chamber. By applying a voltage, an electric field is formed in the chamber transverse to the direction of flow in the chamber. A sample stream containing a mixture of various components capable of electrophoretic separation is injected into the buffer stream so that it flows through the electrophoresis zone. As the sample is carried through the zone, each component of the sample migrates toward the oppositely charged electrode a distance that is dependent upon the size of the component, the viscosity of the carrier liquid and the magnitude of the component charge. This causes like components of the sample to form into bands in the buffer stream across the width of the zone between the electrodes. These separate bands of differing components are collected at the exit end of the electrophoresis zone by means of spatially distinct exit ports whose total flow is commensurate with the total flow of the sample and carrier.

The continuous capillary free flow electrophoretic-based separations take place within a thin chamber confined by an inner surface and an outer surface. A continuous feed of mixed substances or species is injected into a point at one end of the chamber midway between the surfaces. A carrier solution is introduced to fill and flow through the chamber. An electric field is applied uniformly across the chamber, causing the charged sample components to move electrophoretically. Chemical species with different electrical charges, masses or shapes will move at different velocities, and the device is able to make the desired separation based upon these differences in electrophoretic velocities. The separated substances are separated as they flow through the system and may be collected as fractions at separate collecting locations at the outlet end of the chamber. The trajectory of substances through the device depends upon the electrophoretic velocities.

The flow of fluid sweeps the particles through the chamber so that each sample component follows a trajectory defined by the lateral motion induced by the cumulative lateral electrophoretic movement combined with the subsequent flow effects and by the vertical motion induced by the flow of the carrier liquid. Thus, each sample component will exit at the opposite end of the chamber at an angular location depending upon its electrophoretic mobility.

In general, the apparatus includes a separation chamber with an inlet end and an outlet end. The chamber may be lined in glass or other suitable non-reactive material. A charged electrode is in communication with conductive medium and an oppositely charged electrode with conductive medium. The electrodes are electrically connected to a power supply. The apparatus also includes a fresh supply of conductive medium which is fed into the inlet of a tube via conduit. The buffer fills the tube and exits through a conduit into a reservoir. The chamber may have a depth in the range of 1–500 mu m, preferably 25–200 mu m, and most preferably 75–100 mu m. The length of the chamber may be in the range of 1–500 centimeters from the inlet end to the outlet end, preferably 5–100 cm. Apparatus which operate under electric fields of from decades of volts per centimeter up to hundreds of volts per centimeter or more are preferred. Various free-flow electrophoresis apparatuses are well known in the art and some are described in U.S. Pat. Nos. 5,277,774; 5,275,706; 5,139,680; 5,114,555; and 4,698,142, hereby incorporated by reference in their entireties.

Any conventional method of on-line or off-line detection may be used in the invention, including those used in conventional electrophoresis methods. A detection method may be chosen which allows for detection of any physical property of a chemical species. These detection systems include, but are not limited to, absorbance of ultraviolet or visible radiation, fluorescence, refractive index, Raman, mass spectrometry, electrochemical, and conductivity.

The sample or reactant volumes may be introduced by any of the methods employed in electrophoretic systems, including hydrodynamic or electrokinetic. Furthermore, the system can be readily automated for injection with commercially available autoinjectors.

The design parameters which may be varied within any method of the invention include electro-osmotic flow, electrophoretic mobility, nature of the electrophoretic medium, pH, temperature, ionic strength, viscosity, sample volume, electric potential, length of the chamber, detection method, and the concentrations of the analyte species. These parameters may be optimized for any chemical analysis performed according to the invention. Varying one or more of these parameters allows one of skill in the art to exploit a vast number of chemical analyses in the invention, and confers versatility on any method developed in accordance with the invention.

The electrophoretic velocity of a chemical component of the analysis is determined by its electrophoretic mobility in an electric field and the electroosmotic flow. Electroosmotic flow is an inherent factor in the electrophoretic velocity of each chemical species present in the system, and affects the duration of the transport of the analyte to the chamber outlet. Control of electroosmotic flow allows for reproducible separation. The pH of the electrophoretic medium as well as its ionic strength alters the solution flow.

The electrophoretic mobility of the component is affected by the nature of the electrophoretic medium, e.g., pH, ionic strength, and viscosity. An electrophoretic medium, e.g., free solution, sieving gel, partitioning or complexatory additives, or isoelectric focusing medium, may be chosen for physical properties which will selectively impede or enhance the electrophoretic mobilities of certain components of the system. For example, a more viscous medium can increase the molecular drag of the species and, therefore, decrease electrophoretic mobility. In addition, the degree of ionization of charged molecules in the system can be selectively altered by buffering the medium at various pHs and varying the ionic strengths. The electrophoretic medium is critical in the present invention and may include, but is not limited to, free solution, gels, complexatory agents, partitionary additives, and ampholytic species.

The viscosity of the electrophoretic medium may affect the diffusion coefficient for a given chemical species. As the viscosity of the medium increases, the diffusion of the components becomes less pronounced. The viscosity of the medium may be modified according to any parameter known to one of skill in the art, including the following: Non-partitioning additives may be added to the medium, e.g., ethylene glycol or linear polymers.

The volume of sample is chosen in light of other experimental parameters, e.g., the relative electrophoretic velocities of analytes and the concentration of analytes within a zone.

The potential required to impart electrophoretic motion is typically applied across the gel by a high voltage source operated at electric field strengths generally ranging from several tens of volts per centimeter to hundreds of volts per centimeter. The application of the potential can be controlled either via manual operation, a waveform generator, or computer control. The rates of migration of chemical species in electrophoresis are directly proportional to the electric field applied due to electrophoretic and electroosmostic effects. As used herein, low potential refers to approximately 1 to 100 volts/cm; high potential refers to approximately 100 to 300 volts/cm.

The length of the electrophoretic chamber used in combination with the applied potential determines the strength of the electric field and thus also affects the rates of migration of each chiral species. In addition to the overall length of the electrophoretic chamber, the separation length, i.e., the length between the point of introduction of the analyte into the electrophoretic chamber and the position at which the desired analyte exits the chamber is another parameter, which affects the assay.

Electrophoresis typically is performed in a buffered medium. Electrophoretic mobility in solution is determined by the charge density and size of the given species. The parameters of pH and ionic strength are determined by the identity and concentration of the chosen buffered solution. The buffer may alter the degree of ionization of various moieties contained within the chemical components, and thus their electrophoretic mobilities. The type of electrophoretic medium chosen by one of skill in the art allows for control over the electrophoretic velocities of chemical components of the system. A variety of inorganic, organic, and biological buffers throughout the accessible pH range have been utilized in electrophoretic systems.

It will be understood by those skilled in the art that the present methods are useful for enriching and concentrating optical isomers and that in many practical applications complete quantitative isolation of one optical isomer may not be a practical necessity. Thus, the terms "separation" and "separating" are used herein in their accepted sense of enrichment by modification of the optical isomer concentration ratio and do not necessarily imply quantitative isolation. Although the optical isomers present in the mixture may be enantiomers or diastereomers, other facile techniques for separating diastereomers are known. Without limiting the scope of the present invention, therefore, the primary focus of the description set forth herein will be the separation or enrichment of an enantiomer present in a chiral mixture.

In the process of the present invention, a liquid feed mixture is prepared comprising preferably an aqueous solvent and a chiral collector. The sample feed, which may or may not have chiral selector, is introduced through a separate line. Typically, the aqueous solvent is water, but water-miscible components (e.g., alcohols, tetrahydrofuran, acetonitrile and salts) may be present, so long as they do not prevent or interfere with the separation process.

The chiral collector is a chiral compound which is at least partially water soluble and which selectively associates with an optical isomer present in the mixture. Enantioselectivity (or diastereomerselectivity) generally results from a difference in the association energy between the chiral collector and the two enantiomers (or diastereomers).

The chiral collectors may interact with the optical isomers via a combination of ligand exchange interactions, charge-charge interactions, dipolar interactions, pi-pi interactions, steric interactions, hydrophobic interactions, hydrogen-bonding interactions, or other types of interactions known to those of ordinary skill. As such, the chiral collectors have functional groups or a structure which provide at least three points of interaction with the optical isomer of interest. The points of interaction may be provided, for example, by (i) hydrogen-bonding groups such as carbonyl, hydroxyl, amine, sulfoxide and amide groups, with hydroxyl and amine groups being the presently preferred hydrogen-bonding groups, (ii) acidic groups such as carboxylates, sulfonates, sulfates, phosphates, phosphonates, phosphenates, and phenolates with sulfates being the presently preferred acidic groups, (iii) basic groups such as protonated amines which include, for example, ammonium and alkyl and aryl ammonium groups, (iv) dipolar interactive groups such as carbonyl, amide, and sulfonamide groups, (v) aromatic rings (carbo- or heterocyclic, substituted or unsubstituted) which provide pi interaction with the optical isomer of interest, and (vi) a hydrophobic region consisting of one or more non-polar moieties located in close proximity to one another such as a hydrophobic cavity, i.e., a region of the chiral collector which is generally concave in shape (when viewed in three dimensions), is more hydrophobic than the solution in which the chiral collector is dissolved, and is capable of forming a complex with the isomer of interest.

In a preferred embodiment of the present invention, the chiral collector has a sufficient number of the requisite groups or moieties and in the proper orientation such that simultaneous interactions can occur with chiral molecules. Chiral collectors falling within this class include many native and derivatized cyclodextrins, amino acids (native or derivatized), antibiotics (native or derivatized), proteins (native or derivatized), peptides (native or derivatized), carbohydrates (native or derivatized), crown ethers, specially designed synthetic compounds and combinations thereof. In this context, derivatization means attachment of a functional group or moiety which (i) provides one or more points of interaction as described in detail in the paragraph immediately preceding this paragraph.

In general, the amount of chiral collector in the liquid feed mixture is preferably present in a molar excess relative to the optical isomer.

The use of complexatory agents in the electrophoretic medium offers the selective interaction of charged or uncharged reagent species with charged or uncharged solution additives. One of skill in the art may choose a given additive based on its ability to form a complex with an analyte. The complex will then migrate in the electric field with a characteristic mobility. For example, crown ethers and cyclodextrins have been used as additives capable of selectively complexing with chiral compounds in the presence of an applied electric field.

Host-guest enantioselective complexes in the mobile phase are used to separate the individual enantiomers. Systems within this general category include those employing chiral crown ethers and cyclodextrins. Compared to crown ethers, cyclodextrins are relatively inexpensive, and are more readily derivatized. In addition to gamma-cyclodextrin, other chiral selectors known in the art may be used to enhance the chiral separations. For example, the smaller alpha- or beta-cyclodextrins could be advantageously used where a smaller analyte is being separated. Other water-soluble cyclodextrin compounds that may be used for this function include cyclodextrin polymers, carboxylic acid and sulfated, sulfonated, phosphorylated or aminated derivatives of a cyclodextrin, and hydroxypropyl- and hydroxyethyl-derivatives of alpha-, beta-, and gamma-cyclodextrins. Non-cyclodextrin chiral selectors may also be used as enhancers, including chiral crown ethers and bile salts. It is preferred that the chiral collector be stable through the fractionation and separation steps of the present invention to enable recycle and reuse of the chiral collector.

Although temperature of operation is not narrowly critical, lower operating temperatures generally provide greater selectivity. Depending upon the selectivity, therefore, the process may be carried out at room temperature. Run temperatures will range from about 4° C. to 85° C., usually from about 10° C. to 40° C., preferably 20° C.

In general, factors that affect the separation include the following: (a) electrophoretic chamber length, (b) electrophoretic chamber geometry, (c) buffer and sample feed flow rates, (d) concentration of the chiral collector and the chiral mixture, (e) nature of the chiral collector, (f) temperature, (g) pH, (h) reflux time, and (i) the presence of other materials in the sample (e.g., miscible organic solvents, salts, etc.).

Buffers may be simple salts such as phosphate, citrate or borate, or biological buffers such as tricine, MES or TRIS. Buffers effective in antibody complex separation include tricine and NaBorate, at pH ranges of 7–8. For other applications, buffers covering pH ranges from less than 2 up to 12 may be used to achieve the appropriate separations. Change in pH may change the structure or charge on the molecules of interest. Ionic strengths of buffers may be varied to match the conductivity of the analyte and detector. Buffer additives include detergents, clathrates, organic modifiers, metal ions, hydrogen bonding/solubilizing agents, complexing agents, and quaternary amines. Metal ions such as K+, Na+ and Cu+ may be added to change selectivity.

In applying electric current across the solutions undergoing electrophoretic separation in accordance with the invention, the voltage utilized at a minimum is that voltage which will produce a separation in a given solution when applied across the chamber housing the solution. The maximum voltage utilizable is determined by safety. In general, voltages of 20 to 120 volts per centimeter of distance between the electrodes (voltage gradient) are employed.

Buffering agents may also be used for pH stabilization or control of ionic strength, since some molecules tend to bind to particular ions. Examples of other buffers include borates, phosphates, citrates, and carbonates. Still other useful modifiers include alcohol and acetonitrile.

Additional modifying agents may also be used which generally depend on the type of molecule being analyzed, and on how the interaction of the solute with the other compounds is to be altered. Those skilled in the art will appreciate that there are many other useful modifiers that can be used to control or change the nature of the separation process.

EXAMPLES

Capillary electrophoretic studies, using sulfated cyclodextrin as chiral additives, were adapted to classical gel electrophoresis separations and validated by chiral CE.

1. Sulfated Cyclodextrin Results a. Capillary Electrophoresis Results

Stalcup and Gahm found sulfated cyclodextrins (nominal average degree of substitution ~7–10) to be very useful as chiral additives in CE for the enantioseparation of over ninety compounds of pharmaceutical interest. The nonoptimized separations were accomplished at either pH 3.2 or 3.8 with the anode at the detector end of the column. Under these conditions, with minimal electroosmotic flow directed toward the injector and the electrophoretic mobility of the anionic cyclodextrin toward the detector, the analytes with the highest affinity for the cyclodextrin migrate the earliest. In this study, it was reported that the neutral and cationic analytes reached the detector only in the presence of sulfated cyclodextrin. Most of the successfully resolved enantiomers contained basic functionality and a stereogenic carbon. However, this approach was also advantageous for the enantioresolution of two atropisomers, several neutral analytes as well as three anionic analytes. In principle, almost any of the compounds resolved using sulfated cyclodextrin in CE should be amenable to separation according to the present invention.

b. Gel Electrophoresis results

Figure 2:
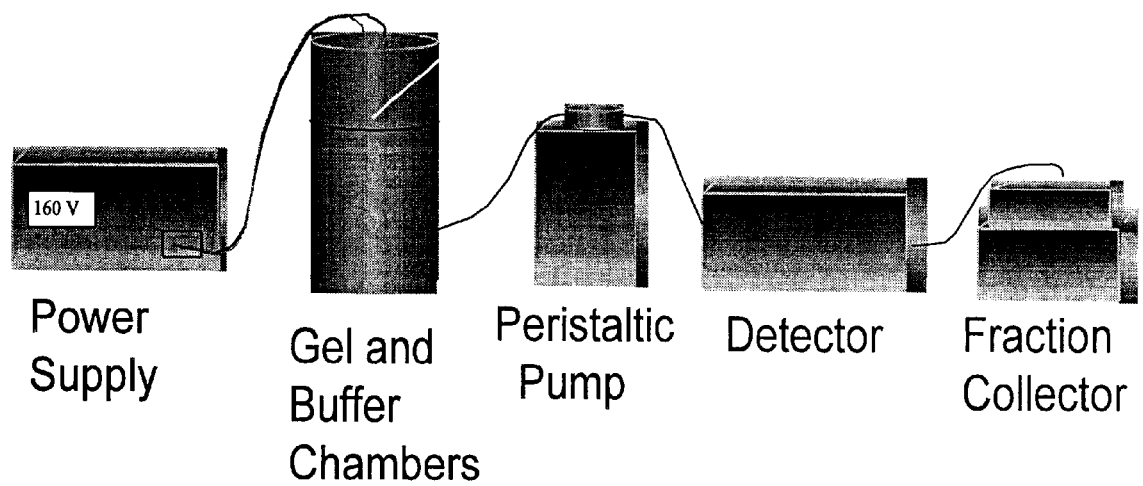
FIG. 2 is a schematic for continuous elution gel electrophoresis apparatus.

Work using classical gel electrophoresis for chiral separations employed a BioRad mini-preparative continuous-elution electrophoresis apparatus (FIG. 1), filled with a 2% agarose gel (medium eeo) and 1–2% free sulfated cyclodextrin. The sample (0.5 mg) was dissolved in a small amount of the pre-gelled agarose solution also containing 1–2% of the free sulfated cyclodextrin and layered on one end of the gel bed after the bed had solidified. In this device, one end of the electrophoretic bed (10 cm×7 mm I.D.) is continually washed with an eluent containing the chiral additive; the eluent is pumped to an HPLC UV detector and then to a fraction collector (FIG. 2). Fractions identified from the UV trace as containing analyte are then subjected to chiral CE analysis to determine the enantiomeric composition of the fractions. Post-run analysis of collected fractions by chiral CE revealed that both enantiomers of terbutaline and piperoxan were obtained with high enantiomeric purity. The buffer pH, ionic strength and sulfated cyclodextrin concentration for the gel electrophoretic run was derived from the CE conditions, demonstrating the synergism of the two electrophoretic techniques. Typical electrophoretic runs, with an applied voltage of 170 V, originally can be done in about 3 hours.

Figure 3:
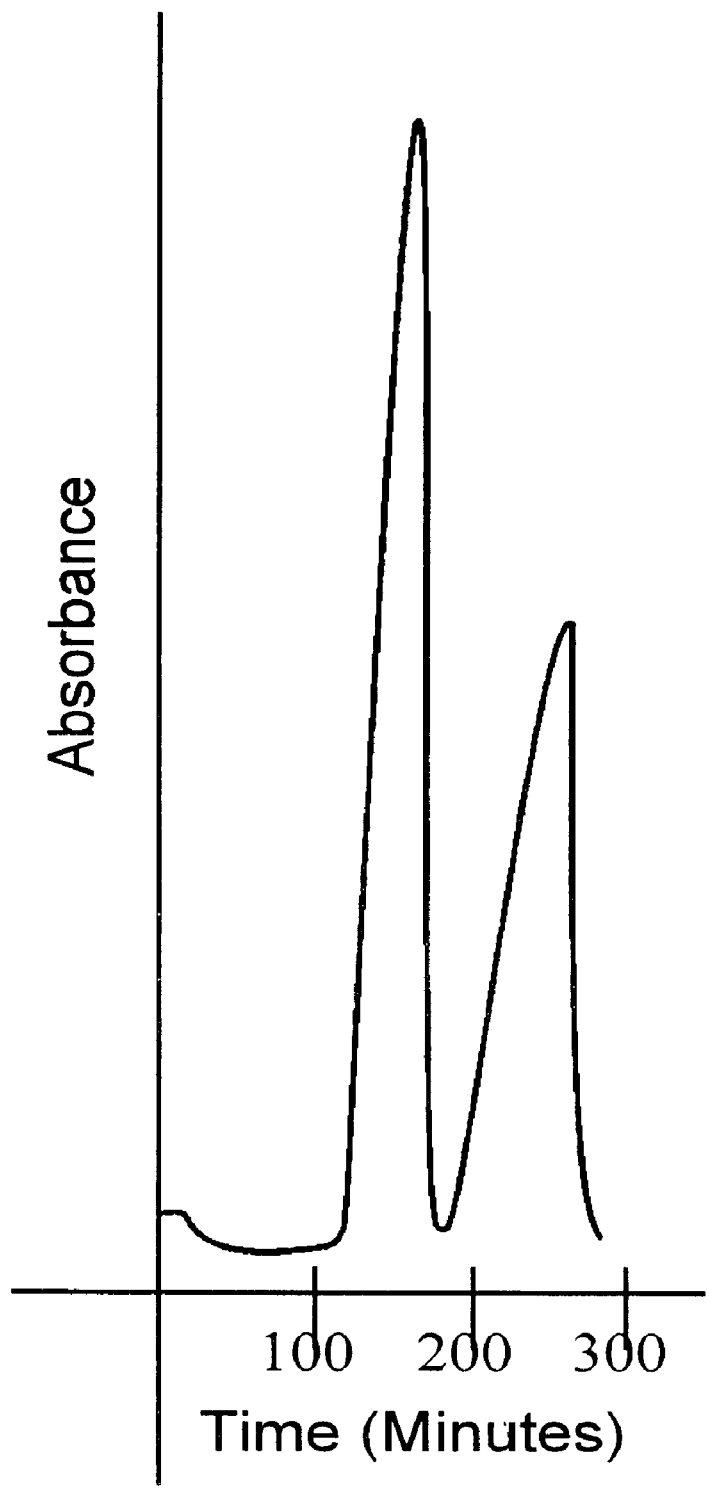
FIG. 3 is a UV trace of 0.5 mg piperoxan loaded onto a 2% agarose gel (10 cm×7 mm I.D.) Using 1% sulfated cyclodextrin, 54 mM citrate, pH 3.

FIG. 3 illustrates the UV trace obtained for 0.5 mg of piperoxan, solubilized in ~0.5 mL of hot agarose/sulfated cyclodextrin solution, loaded onto the mini-preparative system. As can be seen from FIG. 3, baseline resolution ($R_s \approx 2$; $N \approx 200$ for the first peak) is achievable using this approach. The gel-based separation operates on essentially the same principles as the CE method. It is important to note that the experimental conditions allow the gels to be used more than once. The variation in peak elution time, using the same gel for three consecutive runs, was ~±5% for both the early and late eluting peaks. The sulfated cyclodextrin is recovered by simply adding ethanol to the run buffer. Analysis of the sulfated cyclodextrin by CE reveals only slight differences between the cyclodextrin before and after the gel run.

More recently, this work has been further scaled up to a larger preparative system

TABLE 2

Experimental parameters for the mini-prep and preparative gels.

| | Prep | Mini-prep | Ratio |
| --- | --- | --- | --- |
| Cross sectional area | 3.6 cm$^2$ | 0.38 cm$^2$ | 9.5:1 |
| Length | 36 cm | 10 cm | 3.6:1 |
| Current | 65 mA | 12 mA | 5:1 |
| Voltage | 325 V (9V/cm) | 125 V (12.5V/cm) | 2.6:1 (0.7:1) |
| Sample capacity | ~25 mg* | ~1 mg | 25:1 |

Figure 4:
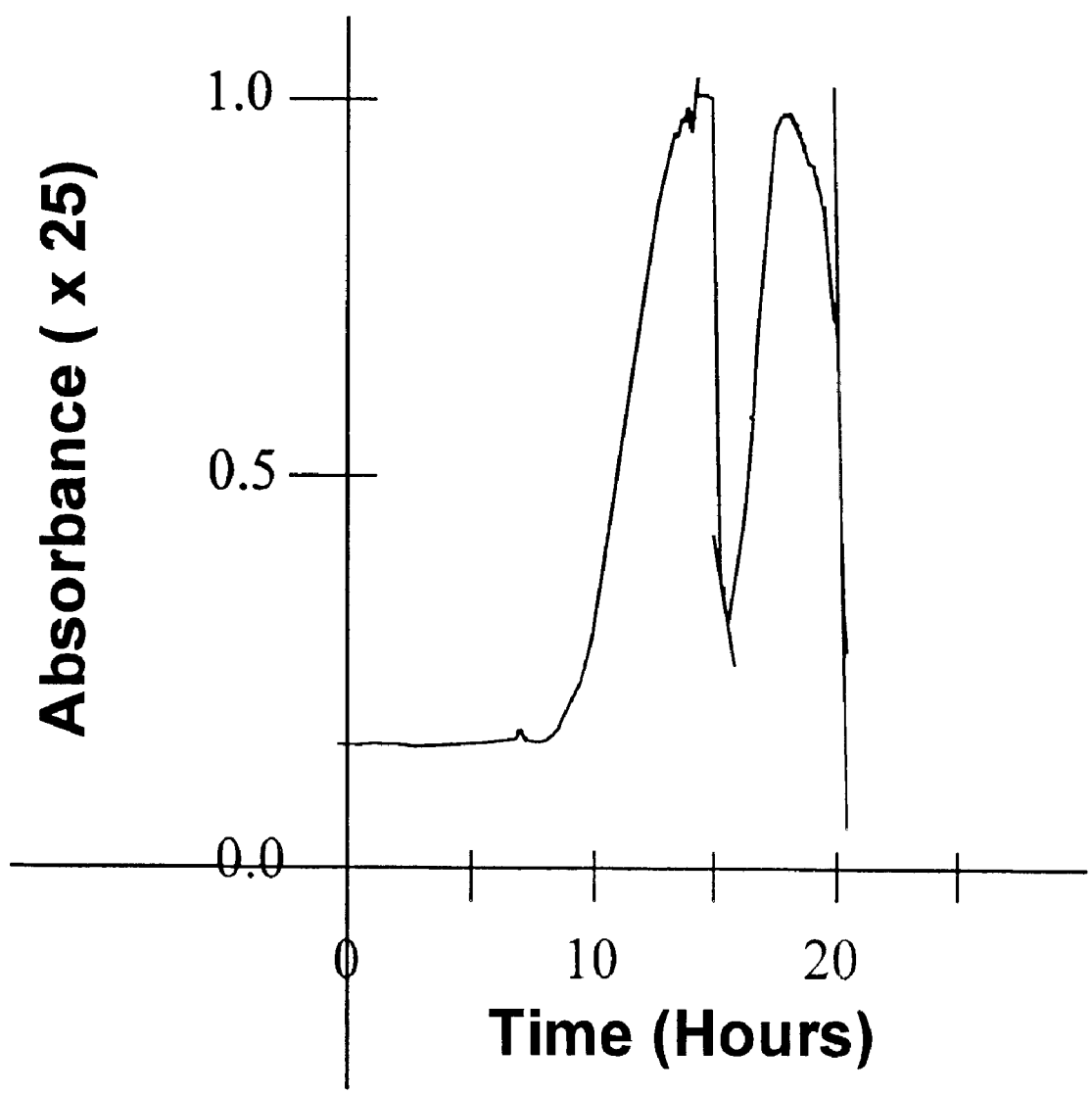
FIG. 4 is a UV trace of 15 mg tetrabutaline loaded onto a 3% agarose gel (36 cm×28 mm I.D.) Using 1% sulfated cyclodextrin, 54 mM citrate, pH 3, on a preparative agarose gel with a run voltage of 320V and a run current of 60–80 mA.

*estimated in which the gel bed is longer and wider (Table 2) than the mini-preparative system. In this apparatus, the gel bed is cast around a ceramic core that runs lengthwise through the center of the gel. Chilled buffer is continuously pumped through a tube in the center of the ceramic core for more efficient cooling than possible with the air-cooled, mini-prep apparatus. This design has significantly increased the sample capacity. FIG. 4 illustrates the UV trace of a run in which the gel was loaded with 15 mg of terbutaline. However, runtimes are prohibitively long.

Example 1

Experimental Design and Methods

The methods and equipment of the examples includes the R&S Technology prototype preparative continuous free flow electrophoresis apparatus, a Bio-Rad BIOFOCUS 3000 and a BIOFOCUS 2000 capillary electrophoresis systems with computer control.

In the preparative continuous free flow electrophoresis apparatus, the electrophoresis chamber is approximately 8 cm in width, 14 cm in length and 3 cm in depth. Capillary spaces are created in the chamber in the interstitial volume between closely aligned capillary TEFLON tubing, aligned parallel to the buffer flow. Cooling water is pumped through these TEFLON tubes to effect cooling while the separation is performed in the spaces between the capillaries. The cooling allows fairly high voltages (e.g., 400 V with currents of ~250 mA) to be well tolerated.

There are seven ports for the continuous introduction of buffer and three sample ports (only one used at a time) for the introduction of the sample stream into the top of the chamber. Dye experiments in the buffer streams indicates surprisingly little turbulence or mixing between adjacent buffer streams. Four additional ports are used to continually flush the electrodes which are isolated from the electrophoresis chamber by a membrane.

The electrodes, which extend the entire length of either side of the electrophoresis chamber are continually washed with fresh buffer. The constant exchange of the electrode buffers allows long runs times using buffers with lower ionic strength (e.g., 10 mM) than are typically used in CE (e.g., 50–100 mM). The various buffer and sample streams are pumped using peristaltic pumps. Typical flow rates for the buffer are 15 mL/min while the sample flow rate is on the order of 0.2–0.3 mL/min.

At the bottom of the preparative continuous free flow electrophoresis chamber, there are forty eight ports which are connected through TEFLON tubing to an array of forty eight sample receptacles.

Example 2

Figure 5:
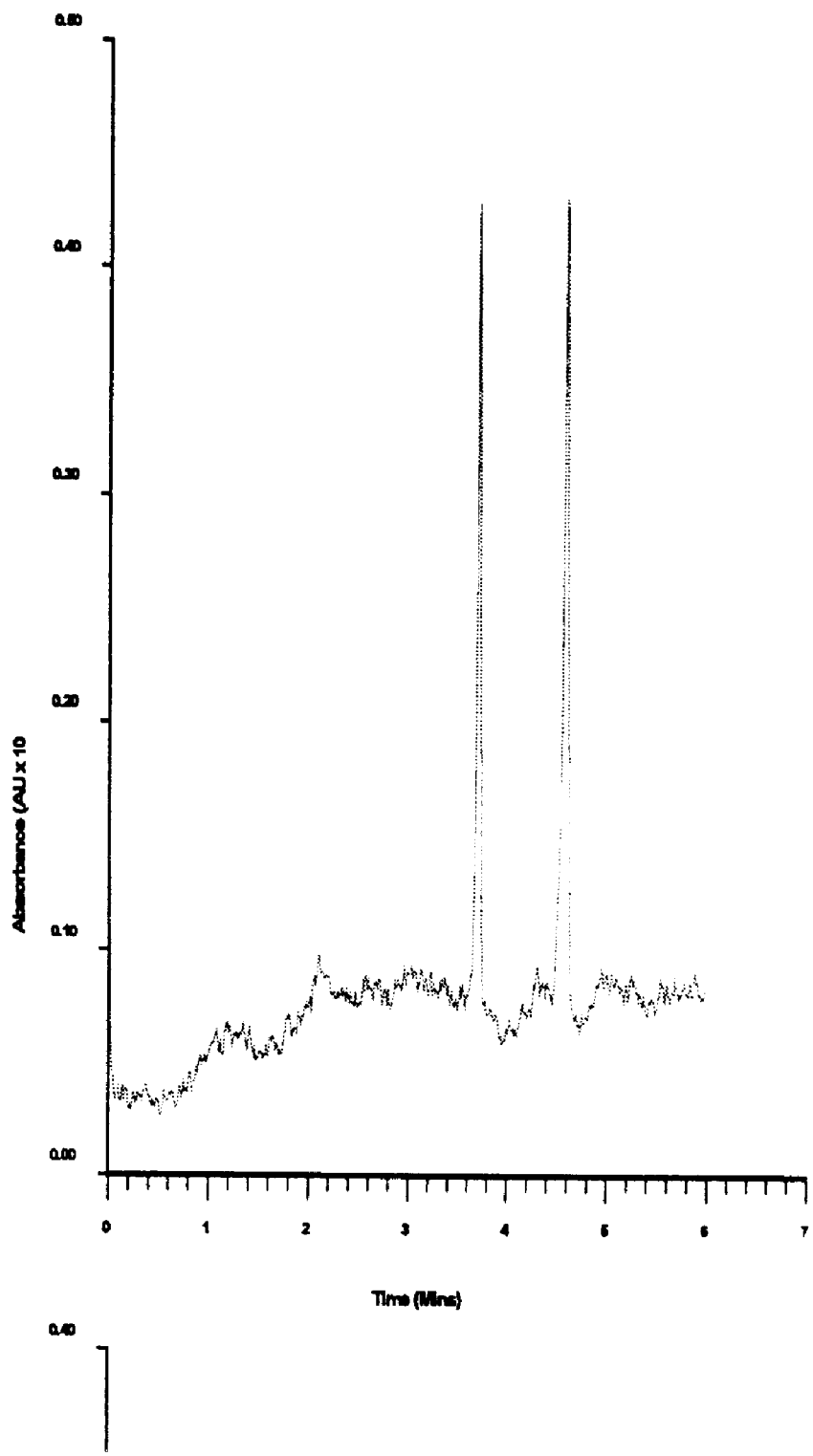
FIG. 5 illustrates an electropherogram of a fraction collected from the continuous free flow electrophoresis system. The original sample contained ~10 mL of 3 mg/mL piperoxan and was processed in 30 minutes.

Implementation of Electrophoretically-driven Chiral Separation Using Cyclodextrins FIG. 5 shows some preliminary results obtained for piperoxan in which sulfated cyclodextrin was only added to the sample stream (flowrate: ~0.3 mL/min) in the continuous free flow electrophoresis apparatus. Analysis by chiral CE of fractions of piperoxan (concentration of sample stream: ~3 mg piperoxan/mL) collected in this initial experiment with 5% sulfated cyclodextrin only in the sample stream (~7 mL of sample solution processed by continuous free flow electrophoresis in ~30 min) showed an enrichment of one enantiomer in some of the fractions and enrichment of the other enantiomer in other fractions.

Figure 6:
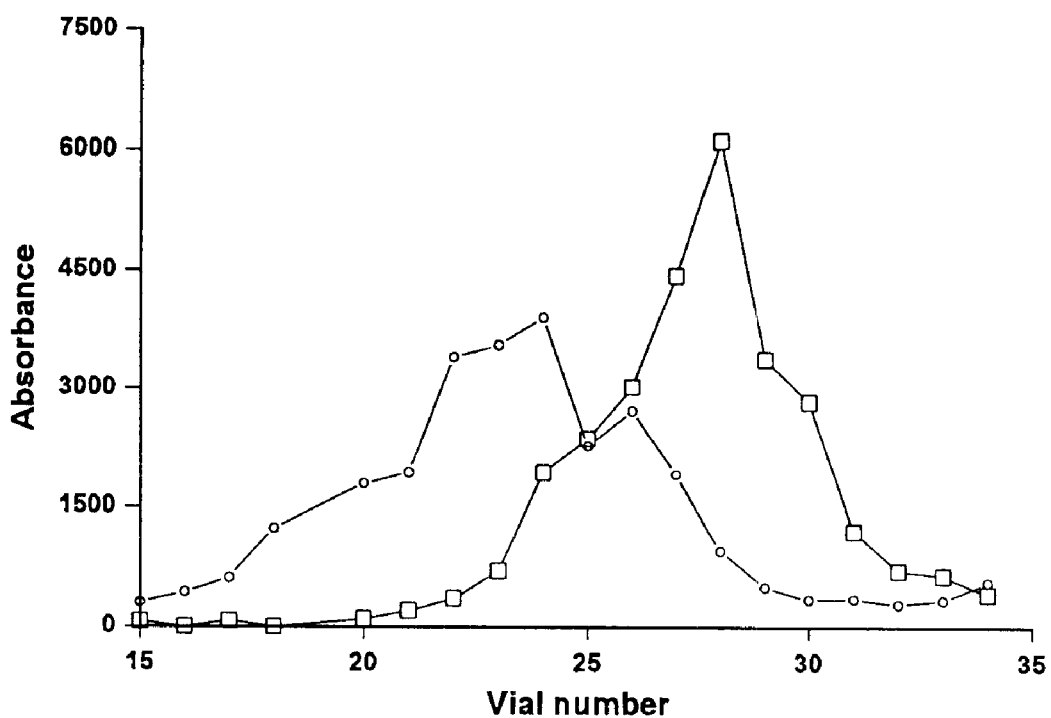
FIG. 6 illustrates a histogram of piperoxan fractions enantioenriched using capillary continuous free flow electrophoresis. Circles and squares are representative of the relative concentrations of each enantiomer in the individual sample vials.

FIG. 6 illustrates a histogram generated for piperoxan from CE analysis of individual fractions collected in the continuous free flow electrophoresis apparatus when 0.5% sulfated cyclodextrin in 10 mM phosphate buffer (~pH 3) was added to all of the buffer streams. As can be seen from the histogram, significant enrichment is obtained for both enantiomers under nonoptimized conditions.

Because there are seven individual run buffer ports, the generation of discontinuities in the pH, density or ionic strength across the chamber can be readily achieved (e.g., isoelectric focusing) and chiral additive may be conserved because it may only be necessary to have the additive in the sample stream or only in the streams directly in contact with the sample stream.

As mentioned previously, it seems likely that analytes which would be most amenable to the proposed electrophoresis method should contain an ionizable moiety which complements the charge on the chiral selector (e.g., sulfated cyclodextrin paired with piperoxan (FIG. 7b) or terbutaline (FIG. 7c)).

Because the sample stream is added to the buffer stream, there may be some flexibility with regard to sample solvent composition (e.g., addition of methanol for neutral molecules). Therefore, low sample solubility in the buffer may not be an issue and in principle, this approach should be generally applicable to any of the structurally diverse compounds successfully enantioresolved by any chiral additives used in CE.

Example 3
Optimization of the Continuous Electrophoresis System

As discussed in the introduction, in preparative continuous free flow electrophoresis, the differential interaction between the various solutes and the electric field produce a lateral displacement of the individual analytes between the two electrodes. The angle of the deflection ($\Theta$) of the solute in the electric field is dependent upon the apparent or intrinsic electrophoretic mobility of the solute ($\mu_i$), the linear velocity of the buffer (v) and the current through the chamber (I) and can be described as:

$$\tan\Theta = \frac{\mu_i i}{q\kappa v} \tag{I}$$

where q is the cross section of the separation chamber and $\kappa$ is the specific conductance of the buffer. It is recognized that this is an empirically-based equation that incorporates a number of simplifying assumptions. Assuming a mobility of $3\times10^{-4}$ cm$^2$/V.sec, a current of 250 mA, a specific conductance of ~1.2 mmho/cm, a cross-sectional area of 24 cm$^2$ (ignoring, for the moment, the cross-sectional area occupied by the tubing) and a flow rate of 15 mL/min yields $\Theta$~14°. For the separation of enantiomers, we are interested in $\Theta_1-\Theta_2$. Using the expression relating the apparent mobility of an analyte to its binding constant with and additive and the concentration of the additive, substituting a=I/q$\kappa$v and using a series expansion of tan $\Theta$, it can be shown that, to a first approximation, the difference in the angle of deflection for the two enantiomers can be expressed as:

$$\Theta_1-\Theta_2 \approx a(\mu_1-\mu_2) \tag{II}$$

$$\Theta_1 - \Theta_2 \approx a\left[\frac{\mu_{f1}+\mu_{c1}K_1[CD]}{1+K_1[CD]} - \frac{\mu_{f2}+\mu_{c2}K_2[CD]}{1+K_2[CD]}\right] \tag{III}$$

where the subscripts f and c refer to the free and complexed analyte, respectively, and the numbered subscripts refer to the two enantiomers, 1 and 2. Because the mobilities of the free enantiomers are the same and assuming, to a first approximation, that the mobilities of the complexes formed by each of the enantiomers with the cyclodextrin are the same, Equation III can be rearranged to Equation IV $$\Theta_1 - \Theta_2 \approx a\left[\frac{[\mu_f-\mu_c][K_1-K_2][CD]}{[1+K_1[CD]](1+K_2[CD])}\right] \tag{IV}$$

which predicts that, as in CE, separation depends upon differences in the mobilities of the free and complexed state and differences in the binding constants, mediated by the dimensions of the chamber and the specific conductance and linear velocity of the buffer. In essence, the linear velocity of the buffer is analogous to the electroosmotic flow in capillary electrophoresis projected orthogonal to the electrophoretic separation. As in CE, under conditions in which the electroosmotic flow ultimately drives everything to the detector, high flow is generally deleterious to the desired separation. Equation IV also implies that there is an optimum concentration, as predicted in CE by Wren and Rowe[1] for CE. Using the same values as above for the cyclodextrin concentration, the specific conductance, dimensions of the chamber (again ignoring the cross-sectional area occupied by the TEFLON tubing), the flow rate and incorporating a difference between the bound and free mobilities of ~6×10$^{-4}$ cm$^2$/V.sec and a difference in the binding constants for the enantiomers of piperoxan of 380 M$^{-1}$, yields a $\Delta\Theta$ of ~0.6°. Note that this value is based on nonoptimized and uniform conditions across the electrophoretic chamber.

As can be seen from equation (IV), several factors need to be considered when optimizing the electrophoretic conditions. First of all, the polyvalency of charged additives contribute to the ionic strength as well as the conductance of the buffer. Fortunately, the TEFLON cooling tubes help dissipate the Joule heating associated with the higher current produced in the presence of the sulfated cyclodextrin. In addition, using low concentrations (e.g., 10 mM) of buffer components with low mobilities (e.g., citrate vs phosphate) and using low concentrations of polyvalent additives (e.g., sulfated cyclodextrin, <1–2%) or only adding charged additives to selected buffer streams should improve the separation by reducing the overall conductance of the buffer.

In the gel and capillary work, a low pH was used to minimize electroosmotic flow when using agarose gels or uncoated fused silica capillaries. However, electroosmotic flow should be less of a consideration in the continuous free flow electrophoresis system because most of the surface area within the chamber is TEFLON. Therefore, buffer selection should be less restrictive than in CE with uncoated columns. Our initial CE investigations employed phosphate buffers. However, organic buffer systems such as citric acid/sodium citrate, acetic acid/sodium acetate or formic acid/sodium formate may present fewer problems in the ultimate removal from the recovered chiral additive than the phosphate buffer; CE and gel results indicate that these are viable buffer systems. Added benefits of the citrate buffer system are the increased viscosity, which may help limit diffusion, and reduced conductivity relative to the phosphate buffer, which may be useful in countering the high currents associated with polyvalent chiral additives. Lowering the buffer stream flow rate should also enhance the separation although the higher diffusion coefficient of the uncomplexed analytes relative to the complexed may limit the extent to which this approach is useful.

With regard to the chiral separation terms in equation IV, Wren and Rowe predicted that the separation was more robust over a wider range of conditions when the binding constants were small. Thus, the addition of a small amount of organic modifier may be of benefit because of the accompanying increased viscosity and lower conductance may also improve the resolution.

Example 4
Sample and Additive Recovery

The sulfated cyclodextrin is readily precipitated from the buffer through the simple addition of ethanol. The recovered cyclodextrin may be subjected to various analytical methods, including CE analysis using inverse detection to determine any perturbation in the composition of the additive and the amount recovered may be quantitated. Once the cyclodextrin is recovered, the solute may be recovered from the buffer using a variety of methods including liquid-liquid extraction or chromatography. Histograms may be generated for the distribution of the enantiomers in the individual receptacles and used to assess the impact of various changes in the protocol on the distribution of the surrogate dye molecules and for separation as well as the resolution of the enantiomers.

The present methods could be used to separate additional analytes and families of analytes (e.g., antihistamines, antimalarials, drug precursors, etc.). Various functionalized cyclodextrns may be used e.g., carboxymethyl-β-cyclodextrin, an aminated β-cyclodextrin and a sulfated hydroxypropyl-β-cyclodextrin. Preliminary results obtained thus far with the carboxymethyl-β-cyclodextrin suggest that its weakly acidic carboxylic acid moieties allow the electrostatic interactions with the analyte (e.g., propranolol, metoprolol, oxprenolol) to be readily mediated by changing the pH. This may offer some intermediate advantages for analytes which are difficult to separate with the strongly acidic sulfated cyclodextrin or the various neutral cyclodextrins that are commonly available. It is believed, however, that the most useful additives will be charged because neutral cyclodextrins may sometimes precipitate from aqueous solution upon complexation.

As is true for capillary electrophoresis and thin layer chromatography, other types of chiral selectors besides cyclodextrins (e.g., chiral selectors based on calixarenes, surfactants or crown ethers) may be used. In addition, chiral separations by continuous free flow electrophoresis may be accomplished in nonaqueous media.

The ability to perform chiral resolutions on the level of mg to g/hour for a large variety of compounds would enable research into the biological implications of chirality to become more routine than is now possible.

We claim:

1. A method for enriching the concentration of an optical isomer in a mixture of optically active isomers, the process comprising:

providing a separation chamber through which at least one separation medium as carrier and a sample medium to be investigated flow at a substantially constant delivery rate from an inlet end to an outlet end thereof, generating an electric field by means of electrodes across the separation chamber to separate spatially the sample medium into fractions, and providing an additive medium to the separation chamber at a predetermined flow rate; and collecting the fractions at a substantially constant outflow rate, wherein the additive medium contains at least one reagent, which associates with at least one of the of optically active isomers.

2. The method of claim 1, wherein the reagent is added in sufficient quantities until effective separation of the charged species occurs downstream from where the mixture was introduced.

3. The method of claim 2, wherein the reagent is a chiral separator.

4. The method of claim 3 wherein the chiral collector has surface-active properties.

5. The method of claim 3, wherein the chiral selector is selected from the group consisting of cyclodextrins, amino acids, antibiotics, peptides, carbohydrates, crown ethers, specially designed synthetic compounds and mixtures and derivatives thereof.

6. The method of claim 5, wherein the buffer flow is in a downward direction.

7. The method of claim 3, wherein the chiral selector is a cyclodextrin selected from the group consisting of alpha-cyclodextrins, beta-cyclodextrins, gamma-cyclodextrins, cyclodextrin polymers, carboxylic acid and sulfated, sulfonated, phosphorylated or aminated derivatives of a cyclodextrin, and hydroxypropyl- and hydroxyethyl-derivatives of alpha-, beta-, and gamma-cyclodextins and mixtures and derivatives thereof.

8. The method of claim 7, wherein the electric field is applied at about right angles to the buffer flow.

9. The method of claim 3, wherein the amount of chiral selector is present in a molar excess relative to the optical isomer.

10. The method of claim 3, wherein said chiral selector comprises a chiral cyclodextrin.

11. The method of claim 3, wherein said chiral selector comprises a crown ether.

12. The method of claim 3, wherein said chiral selector comprises a bile salt.

13. The method of claim 3, wherein the optically active isomer is an enantiomer.

14. The method of claim 3, wherein the optically active isomer is a diastereomer.

15. The method of claim 1 wherein the separation medium contains one or more components selected from the group consisting of free solution, gels, complexatory agents, non-partitioning additives, partitionary additives, ampholytic species and mixtures and derivatives thereof.

16. The method of claim 1 wherein the separation medium is aqueous.

17. The method of claim 16 wherein the separation medium additionally contains one or more water-miscible components selected from the group consisting of alcohols, tetrahydrofuran, acetonitrile salts and mixtures and derivatives thereof.

18. The method of claim 1 wherein the separation medium contains a buffer.

19. The method of claim 18 wherein the buffer is selected from the group consisting of phosphate, citrate, borate, biological, and mixtures and derivatives thereof.

20. The method of claim 18 wherein the separation medium contains one or more a buffer additive selected from the group consisting of detergents, clathrates, organic modifiers, metal ions, hydrogen bonding/solubilizing agents, complexing agents, quaternary amines, metal ions and mixtures and derivatives thereof.

21. The method of claim 1, wherein the delivery of all media to the separation chamber is by means of a volumetric-propulsion pump.

22. The method of claim 1, comprising continuously introducing the mixture through an inlet port.

23. A method for enriching the concentration of an optical isomer in a mixture of optically active isomers, the process comprising:

providing a solution containing the mixture of the optically active isomers and at least one reagent in which the reagent and the optical isomer associate with each other, providing a separation chamber through which at least one separation medium as carrier and a sample medium to be investigated flow at a substantially constant delivery rate from an inlet end to an outlet end thereof, generating an electric field by means of electrodes across the separation chamber to separate spatially the sample medium into fractions, and collecting the fractions at a substantially constant outflow rate.

24. The method of claim 23, wherein the reagent is added in sufficient quantities until effective separation of the charged species occurs downstream from where the mixture was introduced.

25. The method of claim 24, wherein the reagent is a chiral separator.

26. The method of claim 25, wherein the chiral collector has surface-active properties.

27. The method of claim 25, wherein the chiral selector is selected from the group consisting of cyclodextrins, amino acids, antibiotics, peptides, carbohydrates, crown ethers, specially designed synthetic compounds and mixtures and derivatives thereof.

28. The method of claim 27, wherein the buffer flow is in a downward direction.

29. The method of claim 25, wherein the optically active isomer is an enantiomer.

30. The method of claim 25, wherein the optically active isomer is a diastereomer.

31. The method of claim 23, wherein the chiral selector is a cyclodextrin selected from the group consisting of alpha-cyclodextrins, beta-cyclodextrins, gamma-cyclodextrins, cyclodextrin polymers, carboxylic acid and sulfated, sulfonated, phosphorylated or aminated derivatives of a cyclodextrin, and hydroxypropyl- and hydroxyethyl-derivatives of alpha-, beta-, and gamma cyclodextrins and mixtures and derivatives thereof.

32. The method of claim 31, wherein the electric field is applied at about right angles to the buffer flow.

33. The method of claim 23, wherein the amount of chiral selector is present in a molar excess relative to the optical isomer.

34. The method of claim 23, wherein said chiral selector comprises a chiral cyclodextrin.

35. The method of claim 23, wherein said chiral selector comprises a crown ether.

36. The method of claim 23, wherein said chiral selector comprises a bile salt.

37. The method of claim 23, wherein the separation medium contains one or more components selected from the group consisting of free solution, gels, complexatory agents, non-partitioning additives, partitionary additives, ampholytic species and mixtures and derivatives thereof.

38. The process of claim 23, wherein the separation medium is aqueous.

39. The process of claim 38, wherein the separation medium additionally contains one or more water-miscible components selected from the group consisting of alcohols, tetrahydrofuran, acetonitrile salts and mixtures and derivatives thereof.

40. The method of claim 23, wherein the separation medium contains a buffer.

41. The method of claim 40, wherein the buffer is selected from the group consisting of phosphate, citrate, borate, biological, and mixtures and derivatives thereof.

42. The method of claim 40, wherein the separation medium contains one or more a buffer additive selected from the group consisting of detergents, clathrates, organic modifiers, metal ions, hydrogen bonding/solubilizing agents, complexing agents, quaternary amines, metal ions and mixtures and derivatives thereof.

43. The method of claim 23, wherein the delivery of all media to the separation chamber is by means of a volumetric-propulsion pump.

44. The method of claim 23, comprising continuously introducing the mixture through an inlet port.

* * * * *